US011340238B2

(12) United States Patent
Kulshrestha et al.

(10) Patent No.: US 11,340,238 B2
(45) Date of Patent: May 24, 2022

(54) METHOD FOR DETECTING NEUTRALIZING ANTIBODIES AGAINST RECOMBINANT HUMAN INSULIN IN HUMAN SERUM

(71) Applicant: Biocon Limited, Electronic City P.O. (IN)

(72) Inventors: Abhishek Kulshrestha, Dehradun (IN); Ravi Shankar Maurya, Gorakhpur (IN); Sudeep Sabde, Pune (IN); Pallavi Hajela, Lucknow (IN); Pawan Kalani, Jodhpur (IN); Ramakrishnan Melarkode, Bangalore (IN); Narendra Chirmule, Bangalore (IN)

(73) Assignee: BIOCON LIMITED, Electronic (IN)

( * ) Notice: Subject to any disclaimer, the term of this patent is extended or adjusted under 35 U.S.C. 154(b) by 592 days.

(21) Appl. No.: 15/767,595

(22) PCT Filed: Oct. 15, 2016

(86) PCT No.: PCT/IB2016/056191
§ 371 (c)(1),
(2) Date: Apr. 11, 2018

(87) PCT Pub. No.: WO2017/064678
PCT Pub. Date: Apr. 20, 2017

(65) Prior Publication Data
US 2018/0306814 A1 Oct. 25, 2018

(30) Foreign Application Priority Data

Oct. 15, 2015 (IN) .......................... 5528/CHE/2015

(51) Int. Cl.
*G01N 33/74* (2006.01)
*G01N 33/50* (2006.01)
(52) U.S. Cl.
CPC ............. *G01N 33/74* (2013.01); *G01N 33/50* (2013.01); *G01N 33/5005* (2013.01); *G01N 2333/62* (2013.01); *G01N 2333/72* (2013.01); *G01N 2500/10* (2013.01)
(58) Field of Classification Search
CPC ..... G01N 33/74; G01N 33/50; G01N 33/5005
See application file for complete search history.

(56) References Cited

U.S. PATENT DOCUMENTS

| 5,521,082 | A | * | 4/1996 | Lewis | ..................... | C12N 7/00 |
| | | | | | | 435/235.1 |
| 5,856,111 | A | | 1/1999 | Ullrich et al. | | |
| 2010/0204455 | A1 | * | 8/2010 | Gervais | ................. | C07K 16/00 |
| | | | | | | 530/388.1 |

FOREIGN PATENT DOCUMENTS

| WO | 2014/011416 A2 | 1/2014 | | |
| WO | WO-2014011416 A2 | * | 1/2014 | ......... G01N 33/6854 |
| WO | 2015/123315 A1 | 8/2015 | | |
| WO | WO-2015123315 A1 | * | 8/2015 | ......... G01N 33/5306 |

OTHER PUBLICATIONS

Minor et al. "Validation of a Cell-Based Screen for Insulin Receptor Modulators by Quantification of Insulin Receptor Phosphorylation", Journal of Biomolecular Screening 8(4); Apr. 22, 2003. (Year: 2003).*
Minor et al., "Validation of a Cell-Based Screen for Insulin Receptor Modulators by Quantification of Insulin Receptor Phosphorylation", 2003, Journal of Biomolecular Screening 8(4), p. 439-446.*
Dixon, "Measurement of Antibodies to Insulin in Serum", 1974, Clinical Chemistry 20(10), p. 1275-1281.*
Fineberg et al., "Immunogenicity of Recombinant DNA Human Insulin",1983, Diabetologia 25, p. 465-469.*
Rajpathak et al., "The role of insulin-like growth factor-l and its binding proteins in glucose homeostasis and type 2 diabetes", 2009, Diabetes Metabolism Research Review 25(1), p. 3-12.*
Lain et al., "PEG Precipitation: A Powerful Tool for Monoclonal Antibody Purification", 2010, Bipharm International Supplements, https://www.biopharminternational.com/view/peg-precipitation-powerful-tool-monoclonal-antibody-purification, [accessed on Nov. 14, 2020].*
Sommer et al., "Capture and intermediate purification of recombinant antibodies with combined precipitation methods", ePub Oct. 18, 2014, Biochemical Engineering Journal 93, p. 200-211.*
Chappell et al., "Effect of Insulin on Cell Cycle Progression in MCF-7 Breast Cancer Cells", 2001, The Journal of Biological Chemistry 276(41), p. 38023-38028.*
Klein et al., "Insulin Activation of Insulin Receptor Tyrosine Kinase ilnn tact Rat Adipocytes", 1986, The Journal of Biological Chemistry 261(10), p. 4691-4697.*
Ranadevan, "MCF-7 Cell Culture Protocol", 2012, https://www.researchgate.net/post/How-to-culture-MCF7-cells/4f629b687ef068d214000001/citation/download, p. 1-5, [accessed on Nov. 14, 2020].*
Kibbey et al., "Novel Electrochemiluminescent Assays For Drug Discovery", 1999, Journal of Laboratory Automation 5(45), p. 1-4.*
Jung et al., "TRIP-Br1 oncoprotein inhibits autophagy, apoptosis, and necroptosis under nutrient/serum-deprived condition", Aug. 21, 2015, Oncotarget 6(30), p. 29060-29075.*
Usta et al., "Chemically defined serum-free and xeno-free media for multiple cell lineages", Aug. 28, 2014, Annals of Translational Medicine 2(10), p. 1-10.*
Bio-Rad, "Want to Skip RNA Isolation?", 2014, Bio-Rad Laboratories, Inc., https://www.bio-rad.com/webroot/web/pdf/lsr/literature/Bulletin_6604.pdf, p. 1-4, [accessed on Nov. 14, 2020].*

(Continued)

*Primary Examiner* — Robert M Kelly
(74) *Attorney, Agent, or Firm* — Katten Muchin Rosenman LLP

(57) ABSTRACT

The present invention provides an in vitro method for detecting the presence of neutralizing antibodies against recombinant human insulin (rHI) in human serum. It also provides a kit for an in vitro method of detection of the presence of recombinant human insulin (rHI) neutralizing antibodies.

14 Claims, 6 Drawing Sheets

(56) References Cited

OTHER PUBLICATIONS

Figure 1:
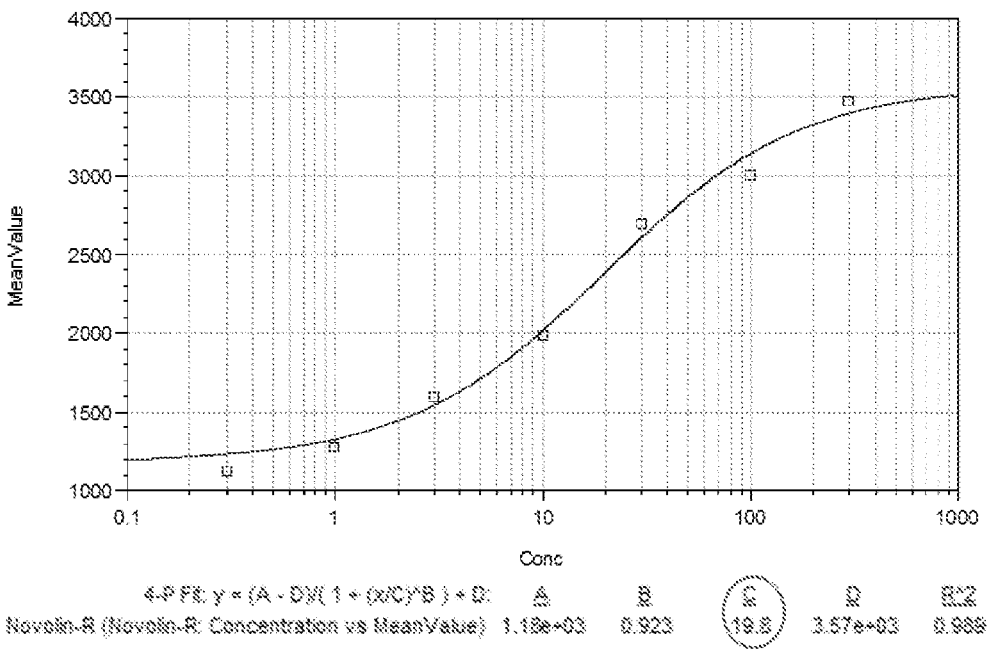

Dozio et al., "Imaging of the Buffering Effect of Insulin Antibodies in the Autoimmune Hypoglycemic Syndrome", Journal of Clinical Endocrinology and Metabolism 83(2), p. 643-648.*
Sen et al., "PGC-1a, a Key Modulator of p53, Promotes Cell Survival", 2011, Molecular Cell 44, p. 621-634.*
Minor LK et al.: "Validation of a cell-based screen for insulin receptor modulators by quantification of insulin receptor phosphorylation", Journal of Biomolecular Screening, Aug. 2003, vol. 8 issue 4, pp. 439-446.
Fineberg SE et al.: "Immunogenicity of recombinant DNA human insulin", Diabetologia, Dec. 1983, vol. 25, isuue 6, pp. 465-469.
Abstract of Sadicka MD et al.: "Kinase receptor activation (KIRA): a rapid and accurate alternative to end-point bioassays", Journal of Pharmaceutical and Biomedical Analysis, May 1, 1999, vol. 19, issue 6, pp. 883-891.
International Search Report for International Application No. PCT/IB2016/056191 dated Jan. 18, 2017.

* cited by examiner

METHOD FOR DETECTING NEUTRALIZING ANTIBODIES AGAINST RECOMBINANT HUMAN INSULIN IN HUMAN SERUM

FIELD OF INVENTION

The present invention relates to an in-vitro method for detecting presence of recombinant drug neutralizing antibodies, in particular neutralizing antibodies against recombinant human insulin, in a serum sample. It also relates to a kit for detecting the presence of neutralizing antibodies against recombinant human insulin in a serum sample.

BACKGROUND OF THE INVENTION AND PRIOR ART

Diabetes, particularly Type I and Type II, is a disorder related to the lack or insufficient production of insulin, a hormone that is secreted by the pancreas. It affects a large number of people worldwide. Management approaches to control Type I and Type II diabetes aim primarily at normalizing blood glucose levels to prevent short- and long-term complications, which is usually by administration of oral medication or injection of insulin or insulin analogs.

Insulin has numerous anabolic effects, including the regulation of carbohydrate, protein, and lipid metabolism. The pleiotropic effects of insulin are mediated upon its binding to the cell surface insulin receptor. The insulin receptor is a hetero-tetrameric tyrosine kinase composed of 2 alpha subunits and 2 beta subunits. Insulin binding to the extracellular alpha subunit initiates receptor dimerization, activation of the intrinsic tyrosine kinase activity of the beta subunit, and trans-phosphorylation of the receptor on several tyrosine residues (Y1146, Y1150, Y1151, Y1316, and Y1322). The activated insulin receptor kinase subsequently phosphorylates numerous intracellular substrates, including the insulin receptor substrate (IRS)-1, IRS-2, and Shc. Specific phosphotyrosine residues provide binding sites for several adaptor proteins, thus setting the stage for the transmission of the insulin signal leading to P13K, Cap-Cbl and MAPK signaling pathway. Activation of the insulin receptor can be measured by quantifying the extent of insulin receptor phosphorylation by direct and indirect methods.

With the advances in DNA technology, it has been possible to produce many recombinant biotherapeutics including recombinant Human insulin (rHI or RHI). Various such rHI formulations are available for the treatment of diabetes. However, such advancement in technology are often accompanied with disadvantages. In other words the biotherapeutics are prone to generate an unwanted immune response in the hosts. The consequences of this immunogenicity range from absence of any effect to transient effect to severe or adverse effect on safety, efficacy and pharmacokinetics of therapeutic protein.

Quite often the immunogenicity has an adverse effect on the efficacy of such therapeutic proteins, particularly when an anti-drug antibody (or ADA) is produced in the patient's body that is neutralizing in nature. As the name suggests, a neutralizing antibody (or NAb) can neutralize activity of therapeutic protein as well as the endogenous counterpart, thus preventing the biotherapeutic from performing its function.

WO/2009/022001 discloses methods based on surface plasmon resonance that uses an acid dissociation step to allow for ADA detection and overcomes drug interference in the presence of drug in serum.

WO/2015/123315 discloses a P and A (PEG and Acid) assay method for detecting ADA by combining biological sample containing potential ADAs with excess drug to form a complex which is then precipitated by PEG followed by basic or acid treatment to dissociate the drug-Ab complex which is then coated on carbon support to immobilize and separate the anti-drug antibody from the complex. Specific detection of the total ADA levels is then performed using labeled drug.

WO/2014/011416 discloses a method for detecting the presence of protein therapeutic neutralizing antibodies in a serum sample, comprising: contacting a population of cells with: i) a serum sample that may contain the protein therapeutic neutralizing antibodies, and ii) the protein therapeutic, wherein the cells comprise a receptor for the protein therapeutic; and detecting a biomarker indicative of binding of the protein therapeutic with the receptor. More particularly, provides a method for detecting the presence of growth factor neutralizing antibodies in a serum sample, comprising: contacting a population of cells with i) a serum sample, and ii) the growth factor, wherein the cells comprise a growth factor receptor; and detecting an amount of a biomarker in the population of cells, wherein the biomarker is indicative of binding of the growth factor to the growth factor receptor, and correlating the amount of the biomarker with the presence of the growth factor neutralizing antibodies.

As with many other human protein therapeutics discussed above, NAb is produced in the patient's body receiving rHI, and they prevent the rHI from binding to the receptors leading to failure in management of diabetes, which could have fatal implications. Moreover, rHI being administered chronically often lifelong has a higher systemic exposure than most other drugs and therefore, incidence of ADA generation is also very high. Consequently, it is extremely essential that methods be available for detection of such NAbs to precisely determine the cause of the drug's failure to act.

Accordingly, there is a need for a highly selective and specific method for detecting the presence of such NAb by analyzing serum samples of diabetic patients receiving rHI.

OBJECTS OF THE INVENTION

An object of the present invention is to provide a highly selective and specific in vitro method for detecting presence of neutralizing antibodies against recombinant Human insulin in a serum sample.

Another object of the present invention is to provide a kit for detection of presence of the neutralizing antibodies.

SUMMARY OF INVENTION

In one aspect the present invention relates to an in vitro method for detecting the presence of rHI neutralizing antibodies in a serum sample, comprising the steps of:
  (a) pre-treating the serum sample; and
  (b) a cell-based assay, wherein it comprises the steps of:
    i. seeding of cells having a receptor for rHI;
    ii. starving the cells;
    iii. stimulating a population of the cells with rHI and the pre-treated serum sample;
    iv. lysing of the cells and preparing a clear lysate; and
    v. evaluating the lysate for phosphorylation of the insulin receptor; and
  (c) correlating the amount of phosphorylation with a floating cut point.

In another aspect the invention relates to a kit for an in vitro method of detection of the presence of recombinant human insulin (rHI) neutralizing antibodies by analyzing a serum sample, comprising the steps of:
(a) pre-treating the serum sample;
(b) a cell-based assay, wherein it comprises the steps of:
   i. seeding of cells having a receptor for rHI;
   ii. starving the cells;
   iii. contacting a population of the cells with rHI and the pre-treated serum sample;
   iv. lysing of the cells and preparing a clear lysate; and
   v. evaluating the lysate for phosphorylation of the insulin receptor; and
(c) correlating the amount of phosphorylation with a floating cut point, wherein the kit comprises PEG 6000 (40%) made in PBS; Dextran Charcoal (3%) made in PBS; Anti-Insulinpolyclonal Antibody (PAb); 600 mM Glacial acetic acid (pH 2.5); 1M Tris Buffer (pH 9.5); Phosphate buffer saline (PBS); and Recombinant Human Insulin.

BRIEF DESCRIPTION OF THE ACCOMPANYING DRAWINGS

The above and other aspects, features, and advantages of certain exemplary embodiments of the present invention will be more apparent from the following description taken in conjunction with the accompanying drawings.

FIG. 1 represents the response of cells to rHI in dose dependent manner and the endpoint is captured as increase in receptor phosphorylation with increase in rHI concentration using ECL as the platform.

Figure 2:
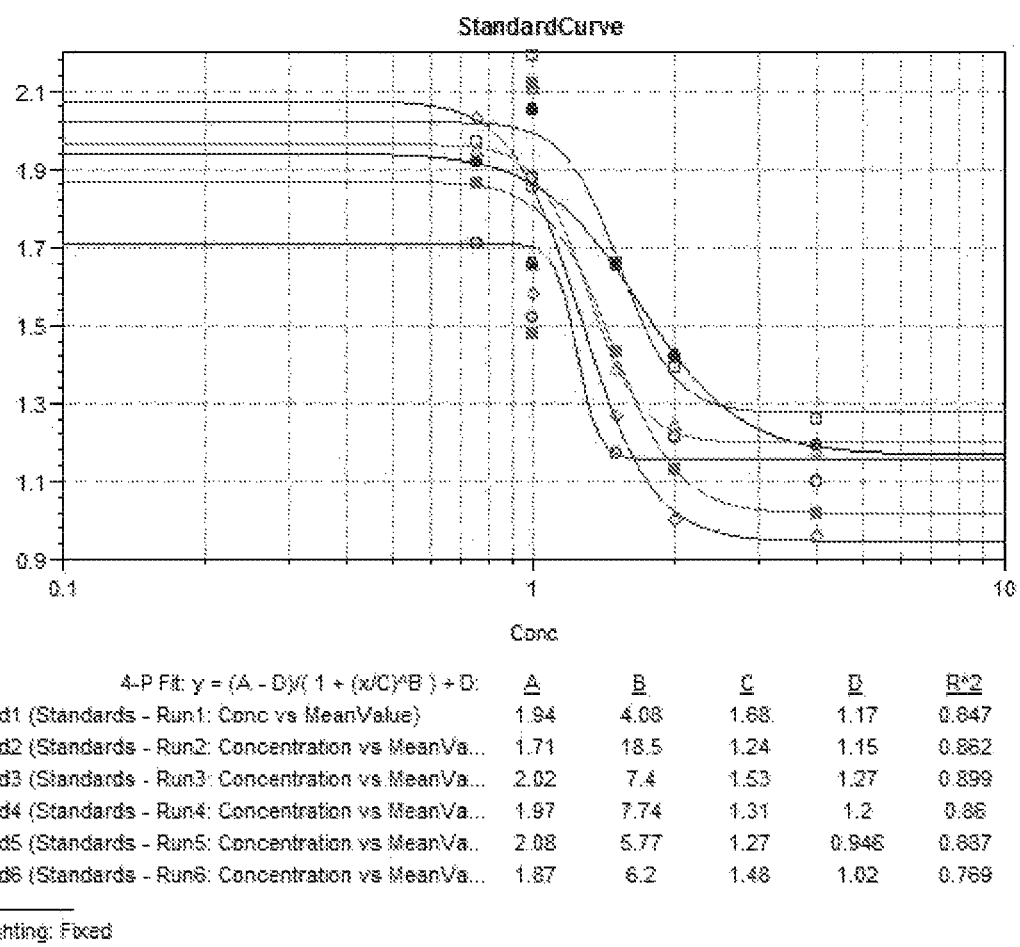
Figure 3:
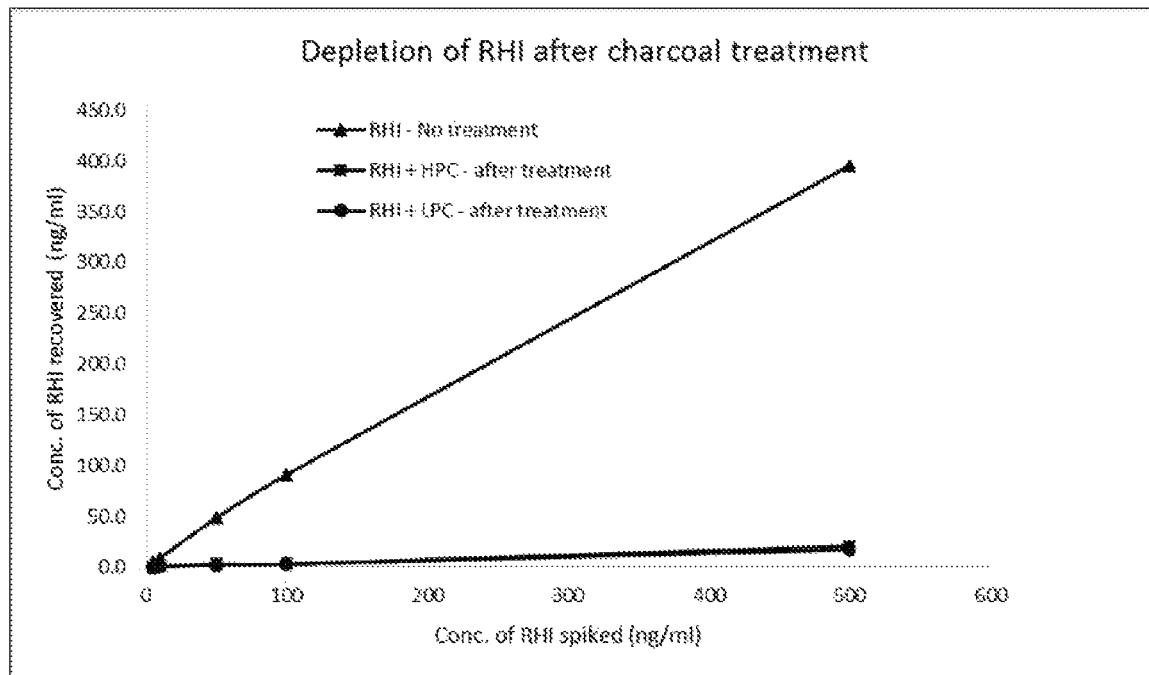
Figure 4:
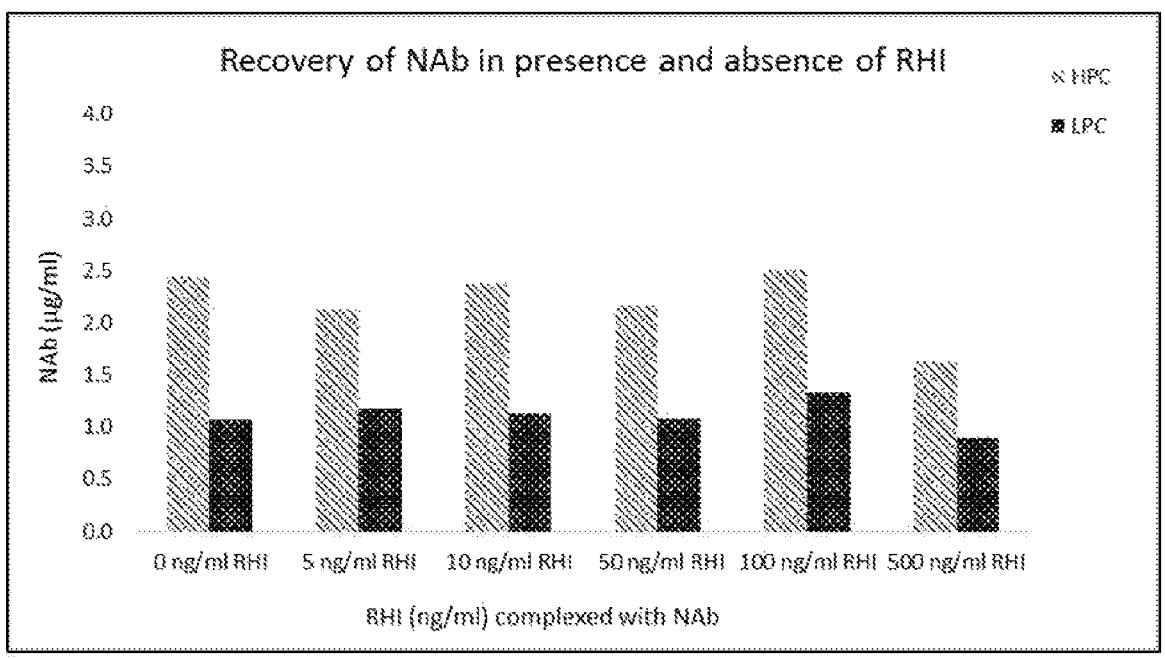
Figure 5:
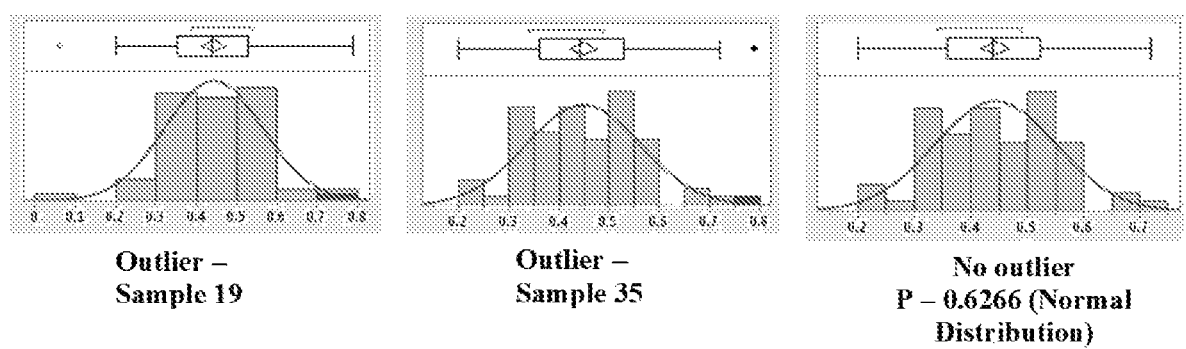
Figure 6:
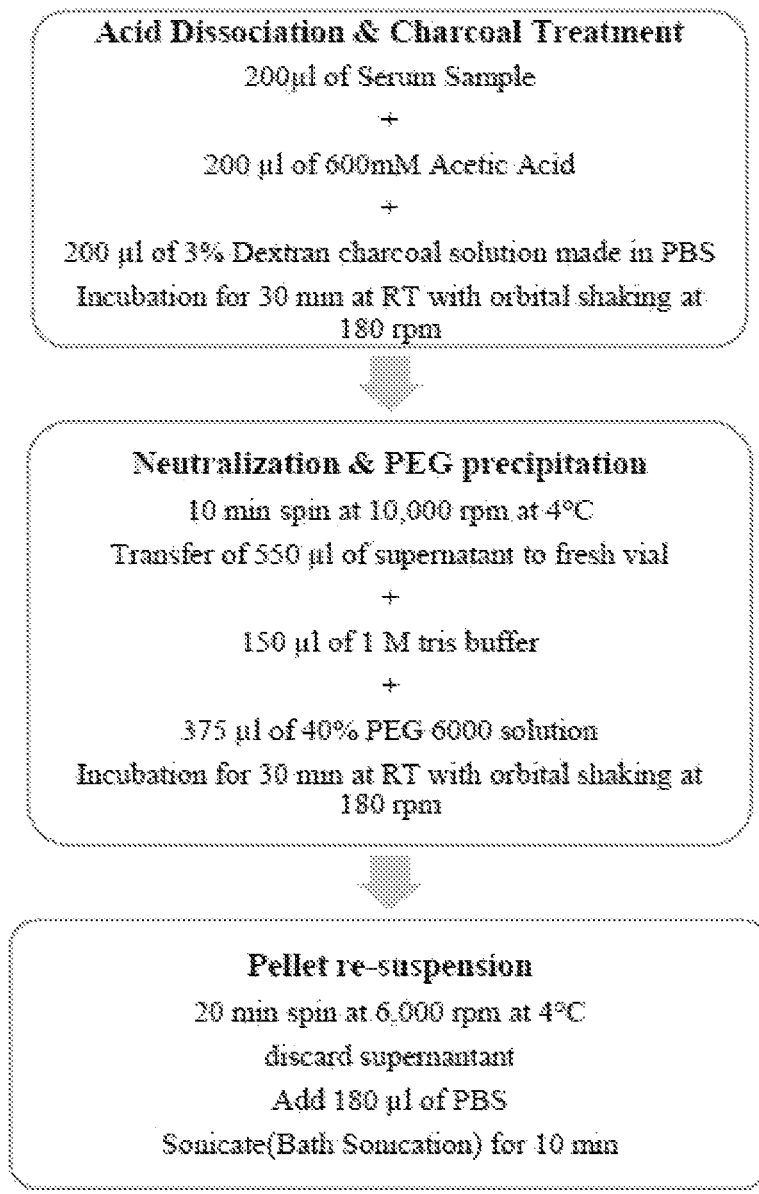
Figure 7:
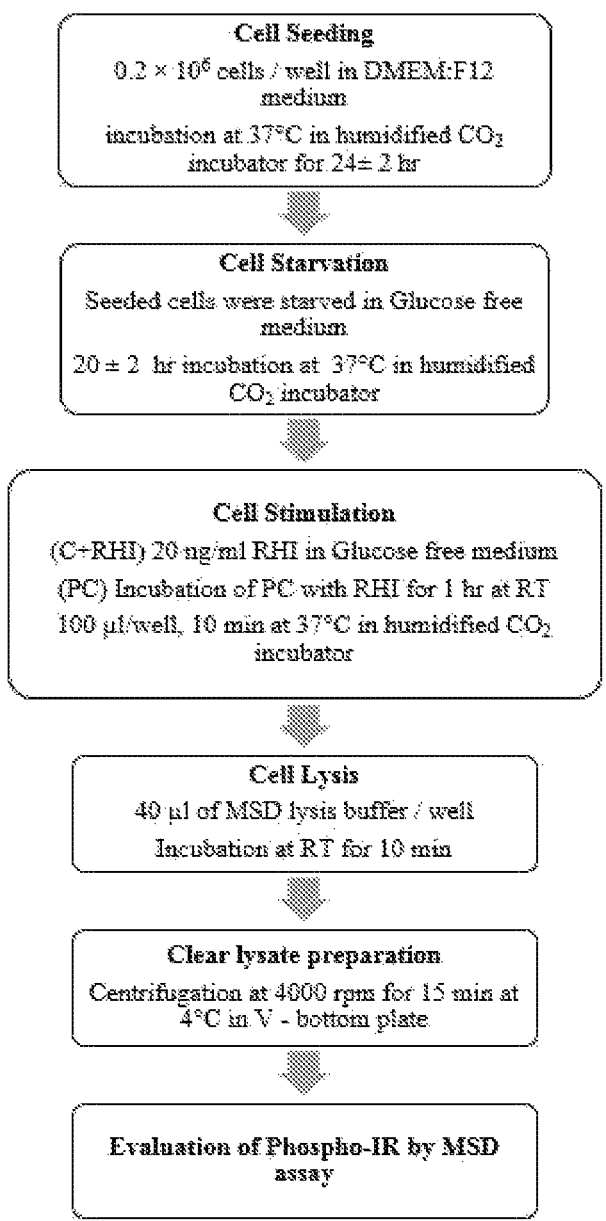

FIG. 2 represents 4 PL curve for each sensitivity run by plotting Mean MoR on the y-axis and concentration on the x-axis FIG. 3 represents depletion of RHI after charcoal treatment FIG. 4 represents recovery of nAb in presence and absence of RHI FIG. 5 represents Outlier analysis and Distribution analysis of cut point data by JMP software FIG. 6 represents the step of pre-treatment of the serum sample FIG. 7 represents the cell based assay step

DETAILED DESCRIPTION OF THE PRESENT INVENTION

The following description with reference to the accompanying drawings is provided to assist in a comprehensive understanding of exemplary embodiments of the invention. It includes various specific details to assist in that understanding but these are to be regarded as merely exemplary. Accordingly, those of ordinary skill in the art will recognize that various changes and modifications of the embodiments described herein can be made without departing from the scope of the invention. In addition, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

"Cells Alone/(CA)" was used as cell control. It represents the basal phosphorylation of IR receptor, cells not stimulated with drug.

"Cells+drug" (C+RHI) was used as the drug control. It represents the phosphorylation of IR receptors in presence of RHI.

"Floating cut point" is the cut point of this assay (Direct neutralizing assay) is the level of response at or below which a sample is defined to be positive and above which it is defined to be negative for neutralizing activity towards the drug product. Floating Cut point is preferred for this assay because of the variable nature of cell based assays.

"Magnitude of response (MoR)" is the ratio of C+RHI/CA. It represents the phosphorylation of IR receptors in presence of a fixed concentration of RHI "MoR Nab" is the ratio of NAb+C+RHI/CA. It represents the inhibition of phosphorylation achieved in presence of NAb.

"% Neutralization" indicates the neutralization of RHI induced phosphorylation of IR receptors. % Neutralization was determined as: (Signal of C+RHI−Signal of NAb)/(Signal of C+RHI−Signal of CA)×100.

"PC samples"—Guinea pig anti RHI antibody was used as a surrogate positive control in the assay. NAb was spiked in Normal pooled human serum or in assay medium to generate positive control samples (PC).

"Precision" measures the degree of reproducibility of the method under normal operating conditions.

"Sensitivity" is the lowest concentration of the positive control yielding a positive assay response or a read out equal to the cut point consistently.

"Specificity" was determined to establish that the positive control only shows a neutralizing response and any other non-specific antibody doesn't show this response.

"Selectivity" is the ability of an analytical method to differentiate and detect the analyte in the presence of other components present in the sample (interfering substances). Selectivity can vary between test samples due to the heterogeneous and polymorphic nature of samples.

The invention is based on the development of specific and selective assays for the measurement of neutralizing antibodies against recombinant human insulin (rHI).

As stated in the background of the invention, patients suffering from Type I and Type II diabetes, particularly patients suffering from Type I are administered insulin or insulin analogs. Oftentimes, the patient's immune system generates antibodies that prevent the insulin or insulin analog from functioning, mostly in cases where the patient is administered rHI. Such antibodies prevent the drug, rHI from binding to the insulin receptors, failing which it is unable to perform its anabolic functions including carbohydrate, protein and lipid metabolism. This leads to inefficient management of diabetes and could even have a fatal effect.

These neutralizing antibodies (NAb) also known as anti-drug antibody prevent the rHI from binding to the insulin receptor and thereby neutralizing the effect of the drug or rHI.

The aforementioned insulin receptor sites on the cells undergo phosphorylation upon binding to the rHI. Accordingly, the phosphorylated insulin receptor acts as a biomarker indicative of binding of the rHI to the receptor. While not being bound by any particular theory, it is believed that the amount of phosphorylated insulin receptor in the cells will increase with increasing exposure to the rHI, but the presence of neutralizing antibodies in a serum sample will lead to a decrease in the amount of phosphorylated insulin receptor. It was found by the present inventors that measurement of a phosphorylated insulin receptor, as opposed to measuring other downstream effects of insulin signaling, leads to a highly specific and accurate evaluation.

The present invention provides in vitro method for detecting the presence of recombinant human insulin (rHI) neutralizing antibodies by analyzing a serum sample, comprising the steps of:
  (a) pre-treating the serum sample; and
  (b) a cell-based assay, wherein it comprises the steps of:
    i. seeding of cells having a receptor for rHI;
    ii. starving the cells;
    iii. stimulating a population of the cells with rHI and the pre-treated serum sample;
    iv. lysing of the cells and preparing a clear lysate; and
    v. evaluating the lysate for phosphorylation of the insulin receptor; and
  (c) correlating the amount of phosphorylation with a floating cut point.

As the term indicates, pre-treatment involves treatment of the serum which is obtained from a patient prior to being assayed. In serum samples the NAb might be present in the form of an immune complex with circulating insulin. The step of pre-treatment of serum samples is necessary to dissociate the NAb-Insulin complex so that complete milieu of neutralizing antibody that is present in the sample can be detected without interference from insulin. Depletion of residual insulin is also important since insulin even in traces can interfere with the cell based assay procedure and result in incorrect and erroneous evaluation.

The inventors found that the pre-treatment ensures dissociation of NAb-insulin complex and is performed by acid treatment of the samples selected from acetic acid and Glycine HCl. The preferred acid is acetic acid. Following acidification, the samples undergo charcoal treatment which adsorbs insulin and leaves NAb free for detection in the cell based assay. Depletion of residual insulin is also important since insulin even in traces can interfere with the cell based assay procedure. The free Nab is precipitated in PEG solution followed by is re-suspension by vortexing or sonication in a sonication bath for about 10 minutes.

The cell based assay step of the invention works on Kinase Receptor Activation (KIRA) principle based on measurement of ligand-induced receptor tyrosine kinase activation in terms of receptor phosphorylation.

Phosphorylated insulin receptor can be detected by any technique known in the art, for example by ECL assay. An electrochemiluminescence (ECL) based assay provides a more quantitative method of detecting the presence of rHI neutralizing antibodies. In such assays upon binding of the therapeutic to its receptor, luminescence is produced during electrochemical reactions in solutions, which is measured and quantified.

The cell lines can be any cells comprising at least one receptor for the rHI being analyzed. Preferred cell lines include cells having high number of receptors on their surface. In certain embodiments, the cell lines are selected from MCF 10A and MCF-7. MCF-7, human mammary adenocarcinoma cell line, being the preferred cell line.

The cell density in some embodiments, in a range of about be $0.05 \times 10^6$ to about $0.5 \times 10^6$ cells per well of 96 wells preferably about $0.2 \times 10^6$ cells per well of 96 wells.

The method comprises seeding the cells in a DMEM:F12 growth medium and incubating them at around 37° C. in humidified air containing about 5% $CO_2$ for a time period of 12 to 16 hours followed by cell starvation. The cells are starved for a period of time ranging from about 18 hours to about 26 hours, preferably about 18 hours to about 22 hours. The starvation is caused by replacing the complete growth medium with Glucose free medium for about 24 hours. The media used for starvation is Glucose free DMEM medium.

The cells are then stimulated in presence of the serum sample and rHI for a period of time ranging from about 5 minutes to about 30 minutes, preferably about 10 minutes at room temperature in suitable media. Simultaneously, the PC is also incubated with rHI from about 30 minutes to about 90 minutes at room temperature, preferably for about 60 minutes followed by 10 minutes at 37° C. in humidified $CO_2$ incubator.

The concentration of rHI effective for binding the insulin receptor and thereby inducing phosphorylation ranges from about 10 ng/mL to about 30 ng/mL preferably 20 ng/mL. FIG. 1 illustrates the dose response curve where RHI has been spiked from 0.3 to 1000 ng/ml in processed normal human serum.

Following stimulation, the cells are lysed. The cells may be lysed while still adhered to the culture plates. Lysis is carried out in presence of commonly known lysis buffers, preferably using lysis buffer while being incubated at room temperature for a time period of about 5 minutes to 30 minutes, preferably 10 minutes.

The cell lysate obtained after centrifugation is evaluated for phosphorylated insulin receptor by ECL based assay. The assay for evaluation of phosphorylation is developed on the MesoScale Discovery (MSD®) platform. MSD®based Insulin Signaling Panel (Phospho Protein) Whole Cell Lysate Kit, has been used. Reagents were used as provided in kit and prepared as per manufacturer's instructions. MSD®based assay was performed using commercial Insulin Signaling Panel (Phospho Protein) Whole Cell Lysate Kit. The Insulin Signaling Panel (Phospho Protein) is a sandwich immunoassay. MSD®) plate is pre-coated with capture antibodies for total IGF-1R, total IR, and total IRS-1 on spatially distinct spots. Cell lysates containing phosphorylated kinase receptors are added on to the wells which are detected by detection antibody—anti-phosphotyrosine conjugated with an electrochemiluminescent compound, Sulfo-Tag label (MSD®).

As represented in FIG. 1 the dose response curve and neutralization of rHI induced phosphorylation of Insulin receptor represents the robust endpoint that the assay employs in form of receptor phosphorylation in presence of Insulin and also the assay platform's sensitive response in detecting presence of any neutralizing antibody.

The detected amount of phosphorylated insulin receptor, in the serum sample can be evaluated compared to the floating cut point for ascertaining the presence of rHI neutralizing antibodies. A floating cut-point is determined based on a negative base pool, and the floating cut point is correlated with the presence of rHI neutralizing antibodies. For example, when a detected amount of phosphorylated insulin receptor in the sample is greater than of the floating cut point, then the serum sample does not contain appreciable quantities of the rHI neutralizing antibodies and when a detected amount of phosphorylated insulin receptor in the sample is lower than of the floating cut point, then the serum sample contains appreciable quantities of the rHI neutralizing antibodies.

In certain embodiments, the method includes a positive control comprising an insulin neutralizing antibody. Accordingly, the method can include comparative analysis of the sample in order to assess the presence of insulin neutralizing antibodies.

The present inventors qualified the Assay and found it to have high specificity and selectivity among others. Various parameters were evaluated for qualification of the assay including robustness and precision. Due to such robustness, sensitivity and precision to detect neutralizing antibodies to administered drug, the present method provides a very efficient tool to predict the safety of the drug during clinical trials and hence will help withstand all regulatory scrutiny and a strategic edge over competitors. It can form a basis for developing a companion diagnostic for rHI as a potential use, which may help a clinician establish if there are pre-existing antibodies to Insulin that could assist in determination of the dosage and course of treatment while prescribing the drug for treatment.

Kits for carrying out the invention method are also contemplated within the scope of the invention. In one embodiment, the kit comprises PEG 6000 (40%) made in PBS; Dextran Charcoal (3%) made in PBS; Anti-Insulin Polyclonal Antibody (PAb); 600 mM Glacial acetic acid (pH 2.5); 1M Tris Buffer (pH 9.5); Phosphate buffer saline (PBS); and Recombinant Human Insulin. Other components of the kits may optionally include reagents and/or instructions for carrying out immunoassays.

The means by which kit can be performed and analyzed can be readily understood in view of the disclosure made herein.

EXAMPLES

Example 1

Pre-Treatment of Sample

The serum sample was treated with 600 mM Acetic acid. Depletion of circulating insulin by 3% Dextran charcoal solution and incubated for a period of about 30 minutes at room temperature and orbital shaking at 180 rpm. It is followed by a 10 minute spin at 10,000 rpm at 4° C., thereafter transferring the supernatant. 150 µl of I M tris buffer, 375 µl of 40% PEG 6000 solution are added to the 550 µl supernatant. This was incubated for about 30 minutes at room temperature with orbital shaking at 180 rpm. Supernatant of PEG precipitated samples was evaluated for presence of NAb which indicated no loss during PEG precipitation. Re-suspension of pellet at 6000 rpm at 4° C. for about 20 minutes in 180 µl of PBS solution was performed by 10 minutes of sonication in sonication bath.

Recovery of NAb after sample processing was consistent and ranged between 50-70%.

FIG. 6 is a schematic representation of the pre-treatment step of the method.

Example 2

Cell Based Assay of Sample

MCF-7 cells were seeded in a 96-well plate in complete growth medium and allowed to adhere to the surface for 14±2 hrs. On the second day, adhered cells were kept for starvation by replacing the complete growth medium with Glucose free DMEM medium (without FBS and RHI) for 20±2 hrs. On third day, Glucose free medium is removed and samples are added to the plate as per the experiment design. After a brief stimulation period of 10 mins, cells are lysed and cell lysate is evaluated for phosphorylated insulin receptor by MSD based phosphoprotein signaling panel kit (FIG. 2)

Example 3

Evaluation of Neutralization of the IR Receptor Phosphorylation with Commercial Antibodies at a RHI Concentration of 0.1 µg/ml Cells were seeded at $0.5 \times 10^6$ cells per well seeding density. Two concentrations of rHI were used for stimulation of cells which were 1 and 0.1 µg/ml. Three available Anti RHI antibodies were evaluated for the neutralization of IR phosphorylation. Two antibodies were obtained from commercial sources viz. Peninsula and Invitrogen respectively while third was in-house generated antibody. All the antibodies were evaluated at 2, 1 and 0.5 µg/ml concentrations.

TABLE 1

Evaluation of neutralizing response at 0.1 µg/ml RHI level with commercial antibodies

| | RHI - 0.1 µg/ml | | | | | |
|---|---|---|---|---|---|---|
| | Peninsula Anti RHI | | In-house Anti RHI | | Invitrogen Anti RHI | |
| NAb | Signa | % Neutralizatio | Signa | % Neutralizatio | Signa | % Neutralizatio |
| 2000 | 403 | 74 | 325 | 98 | 581 | 19 |
| 100 | 499 | 44 | 457 | 57 | 592 | 16 |
| 500 | 570 | 22 | 545 | 30 | 618 | 8 |
| Cells | | | | 317 | | |
| Cells+ | | | | 281 | | |
| Cells+ | | | | 643 | | |
| MoR | | | | 2.03 | | |

As observed, neutralization of RHI induced phosphorylation occurs.

Example 4

The inventors evaluated the neutralizing activity of Anti RHI antibody in normal pooled human serum Anti RHI antibody was spiked in serum and pre-treated according to Example 1. Processed NAb sample was evaluated in the assay as described in Table 2.

TABLE 2

Experimental conditions to evaluate the neutralizing activity of Anti RHI antibody in the NAb assay

| Cell seeding | Seeding density | $0.2 \times 10^6$ cells per well |
| --- | --- | --- |
| | Medium | DMEM:F12 |
| | Incubation | 22 ± 2 hrs at 37° C., 5% CO2 incubator |
| Starvation | Medium | Glucose free DMEM |
| | Incubation | 20 ± 2 hrs at 37° C., 5% CO2 incubator |
| Stimulation of cells | RHI | 10 ng/ml, 20 ng/ml and 30 ng/ml |
| | Medium | Glucose free DMEM |
| | Incubation | 10 min at 37° C., CO2 incubator |
| RHI - Anti RHI Incubation | Volumes | 60 µl/well of RHI and Anti RHI respectively |
| | Incubation | 1 hr at RT |
| Lysis of cells | Lysis Buffer | MSD Lysis Buffer, prepared as per manufacturer's instructions |
| | Exposure | 40 µl/well, 10 min at RT |

The neutralization response was evaluated at 10 and 20 ng/ml concentrations of RHI. NAb spiked in assay medium was used as control in the assay.

Result: Neutralization of IR phosphorylation by NAb spiked in Assay medium—

TABLE 3

Dose dependent neutralization of RHI stimulated IR phosphorylation in assay medium

| | RHI (10 ng/ml) | | RHI (20 ng/ml) | |
| --- | --- | --- | --- | --- |
| NAb (µg/ml) | Signal | % | Signal | % |
| 2 | 339 | 95 | 663 | 80 |
| 1.5 | 408 | 88 | 883 | 68 |
| 1 | 607 | 68 | 1421 | 40 |
| C + RHI | 1268 | | 2182 | |
| CA | 292 | | 272 | |
| MoR | 4.34 | | 8.01 | |

Neutralization of IR phosphorylation by NAb spiked in Serum—

TABLE 4

Dose dependent neutralization of RHI stimulated IR phosphorylation in processed serum

| | RHI 10 ng/ml | | RHI 20 ng/ml | |
| --- | --- | --- | --- | --- |
| NAb (µg/ml) | Signal | % Neutralization | Signal | % Neutralization |
| 2 | 3600 | 49 | 3391 | 79 |
| 1.5 | 3463 | 58 | 3671 | 70 |
| 1 | 3821 | 36 | 4601 | 37 |
| 1.5 + 5 ng/ml RHI | 2845 | 96 | 3409 | 79 |
| 1.5 + 20 ng/ml RHI | 3330 | 66 | 4102 | 54 |
| C + RHI | 4403 | | 5636 | |
| CA | 2773 | | 2811 | |
| MoR | 1.59 | | 2.01 | |

Consistent results are observed. Stimulation of cells with RHI was selected at 20 ng/ml level.

Example 5

To evaluate dose dependent response of RHI on cells in processed serum matrix and select the concentration of RHI for determining neutralizing response of Anti RHI antibodies Normal pooled human serum was processed as per the sample pretreatment procedure as recited in Example 1. Range of RHI was prepared from 0.3 to 1000 ng/ml and added to starved cells ($0.2 \times 10^6$ cells per well). Cell lysates were analyzed in MSD assay. Mean MSD data is reported in below table 5 and FIG. 1.

TABLE 5

Dose dependent response of RHI spiked in processed serum matrix

| RHI (ng/ml) | MSD signal | MoR |
| --- | --- | --- |
| 1000 | 4737 | 3.66 |
| 300 | 3463 | 2.68 |
| 100 | 2996 | 2.31 |
| 30 | 2688 | 2.08 |
| 10 | 1977 | 1.53 |
| 3 | 1588 | 1.23 |
| 1 | 1269 | 0.98 |
| 0.3 | 1116 | 0.86 |
| Cells Alone | 1294 | |

It was observed that cells alone was lesser than that observed in the previous example. Dose dependent response of RHI was observed on cultured cells as illustrated in FIG. 1. EC50 was 19.8 ng/ml which was similar 20 ng/ml RHI concentration selected in the previous experiment.

Determination of Normalization factor for Floating Cut Point:—

Experimental details: Cut point was determined using thirty six normal human individual serum samples in a balanced design. Two analysts (A1 and A2) evaluated the samples on three different days with each analyst analyzing the sample once. The cut point determination was performed according to the design as referenced below. Therefore, total of 72 (36×2) data points were collected for determination of cut point.

Each sample was analyzed in presence and absence of 20 ng/ml of RHI and cut point was reported in terms of magnitude of response (ratio of with drug and without drug). Two replicate samples of normal pooled human serum (NSB) were included in each run in order to determine the negative control level for that plate.

Magnitude of response (MoR) was determined for each individual sample by dividing the signal of with drug sample to without drug sample. LOG of MoR was determined and data set was subjected to analysis by JMPv 11.2 software.

i. The data was evaluated for outliers by box plot analysis. Samples 19 and 35 were identified as outliers and therefore, excluded from the further analysis (FIG. 5).
ii. Distribution of data set was evaluated after exclusion of outliers, data set was found to be normally distributed (FIG. 5).
iii. Parametric approach for calculation of cut point was applied by using the formula Mean−2.33×SD.
iv. Antilog of cut point was determined.
v. Mean NSB was determined across 6 runs.
vi. Multiplicative normalization factor (NF) was determined by using the formula Cut point/Mean NSB Cut point data and data analysis is presented in tables 6 to 8.

Floating cut point was determined by multiplying mean NSB with normalization factor.

TABLE 6

Normal individual serum sample data for cut point

| | A1 | | | | | A2 | | |
|---|---|---|---|---|---|---|---|---|
| Individual sample # | w/drug | w/o drug | Ratio | LOG ratio | Individual sample # | w/drug | w/o drug | Ratio | LOG ratio |
| 1 | 9114 | 3188 | 2.86 | 0.46 | 37 | 7660 | 3505 | 2.19 | 0.34 |
| 2 | 9340 | 2998 | 3.12 | 0.49 | 38 | 8452 | 3846 | 2.20 | 0.34 |
| 3 | 9753 | 3564 | 2.74 | 0.44 | 39 | 8170 | 3703 | 2.21 | 0.34 |
| 4 | 7915 | 3174 | 2.49 | 0.40 | 40 | 9154 | 3699 | 2.47 | 0.39 |
| 5 | 6446 | 2448 | 2.63 | 0.42 | 41 | 6378 | 1851 | 3.45 | 0.54 |
| 6 | 7659 | 2256 | 3.40 | 0.53 | 42 | 7567 | 2395 | 3.16 | 0.50 |
| 7 | 8523 | 2531 | 3.37 | 0.53 | 43 | 7204 | 2271 | 3.17 | 0.50 |
| 8 | 7363 | 1937 | 3.80 | 0.58 | 44 | 5804 | 1834 | 3.16 | 0.50 |
| 9 | 8886 | 3059 | 2.91 | 0.46 | 45 | 7170 | 2321 | 3.09 | 0.49 |
| 10 | 7715 | 3688 | 2.09 | 0.32 | 46 | 6793 | 2493 | 2.72 | 0.44 |
| 11 | 9218 | 4232 | 2.18 | 0.34 | 47 | 7986 | 3237 | 2.47 | 0.39 |
| 12 | 8079 | 3753 | 2.15 | 0.33 | 48 | 7943 | 3867 | 2.05 | 0.31 |
| 13 | 5360 | 1168 | 4.59 | 0.66 | 49 | 5117 | 2014 | 2.54 | 0.40 |
| 14 | 3889 | 1230 | 3.16 | 0.50 | 50 | 4932 | 1520 | 3.24 | 0.51 |
| 15 | 3935 | 1133 | 3.47 | 0.54 | 51 | 4806 | 1735 | 2.77 | 0.44 |
| 16 | 3894 | 1064 | 3.66 | 0.56 | 52 | 4466 | 1882 | 2.37 | 0.38 |
| 17 | 5018 | 2312 | 2.17 | 0.34 | 53 | 5591 | 3559 | 1.57 | 0.20 |
| 18 | 3345 | 1274 | 2.63 | 0.42 | 54 | 5483 | 2232 | 2.46 | 0.39 |
| 19* | 4287 | 3723 | 1.15 | 0.06 | 55 | 4766 | 1839 | 2.59 | 0.41 |
| 20 | 4958 | 1362 | 3.64 | 0.56 | 56 | 5160 | 2180 | 2.37 | 0.37 |
| 21 | 4194 | 1408 | 2.98 | 0.47 | 57 | 5125 | 1986 | 2.58 | 0.41 |
| 22 | 3845 | 1056 | 3.64 | 0.56 | 58 | 4048 | 1324 | 3.06 | 0.49 |
| 23 | 3442 | 744 | 4.63 | 0.67 | 59 | 3426 | 930 | 3.69 | 0.57 |
| 24 | 3803 | 1175 | 3.24 | 0.51 | 60 | 4111 | 2565 | 1.60 | 0.20 |
| 25 | 6112 | 3033 | 2.02 | 0.30 | 61 | 5583 | 2077 | 2.69 | 0.43 |
| 26 | 6792 | 2496 | 2.72 | 0.43 | 62 | 3700 | 1673 | 2.21 | 0.34 |
| 27 | 5775 | 1526 | 3.78 | 0.58 | 63 | 2724 | 1017 | 2.68 | 0.43 |
| 28 | 5879 | 1711 | 3.44 | 0.54 | 64 | 3045 | 1580 | 1.93 | 0.29 |
| 29 | 6713 | 2871 | 2.34 | 0.37 | 65 | 3516 | 2057 | 1.71 | 0.23 |
| 30 | 6589 | 2024 | 3.26 | 0.51 | 66 | 3125 | 1411 | 2.21 | 0.35 |
| 31 | 5784 | 1112 | 5.20 | 0.72 | 67 | 2233 | 726 | 3.07 | 0.49 |
| 32 | 5342 | 1568 | 3.41 | 0.53 | 68 | 3357 | 1377 | 2.44 | 0.39 |
| 33 | 6029 | 1695 | 3.56 | 0.55 | 69 | 2593 | 1121 | 2.31 | 0.36 |
| 34 | 6027 | 1824 | 3.30 | 0.52 | 70 | 2627 | 1281 | 2.05 | 0.31 |
| 35* | 5520 | 898 | 6.15 | 0.79 | 71 | 2065 | 680 | 3.04 | 0.48 |
| 36 | 5978 | 1528 | 3.91 | 0.59 | 72 | 2423 | 1108 | 2.19 | 0.34 |

TABLE 7

NSB data for determination of normalization factor

| | | A1 | | | A2 | | |
|---|---|---|---|---|---|---|---|
| | NSB Sample # | w/drug | w/o drug | Ratio | w/drug | w/o drug | Ratio |
| Run-1 | 1 | 7897 | 3467 | 2.28 | 6110 | 3021 | 2.02 |
| | 2 | 8961 | 3781 | 2.37 | 5637 | 3011 | 1.87 |
| Run-2 | 1 | 3489 | 1786 | 1.95 | 3549 | 2053 | 1.73 |
| | 2 | 4359 | 1786 | 2.44 | 3254 | 1870 | 1.74 |
| Run-3 | 1 | 8280 | 3054 | 2.71 | 8542 | 4010 | 2.13 |
| | 2 | 7962 | 3105 | 2.56 | 8143 | 3626 | 2.25 |

TABLE 8

Determination of cut point and normalization factor Analysis at 1% false positive rate

| | |
|---|---|
| Mean (log) | 0.44 |
| SD (log) | 0.11 |
| Cut point (log) | 0.19 |
| Cut point (Antilog) | 1.57 |
| Mean NSB | 2.17 |
| Normalization factor | 0.72 |

Determination of Assay Sensitivity:

To establish assay sensitivity, 6 dilutions of positive control antibody were prepared from 4 µg/mL to 0.5 µg/mL in normal pooled human serum. Sensitivity was determined from six independent assay runs on three separate days according to the design as presented below in Table 9.

TABLE 9

Compiled data for determination of sensitivity

| NAb (µg/ml) | Run-1 | Run-2 | Run-3 | Run-4 | Run-5 | Run-6 |
|---|---|---|---|---|---|---|
| 4 | 1.19 | 1.10 | 1.26 | 1.18 | 0.96 | 1.02 |
| 2 | 1.42 | 1.21 | 1.39 | 1.25 | 1.00 | 1.13 |
| 1.5 | 1.65 | 1.17 | 1.66 | 1.39 | 1.27 | 1.43 |
| 1 | 1.66 | 1.52 | 1.85 | 1.66 | 1.58 | 1.48 |
| 0.75 | 1.92 | 1.71 | 1.97 | 1.95 | 2.03 | 1.86 |
| 0.5 | 2.05 | 1.88 | 2.19 | 2.11 | 2.11 | 2.12 |
| FCP | 1.71 | 1.57 | 1.59 | 1.57 | 1.94 | 1.59 |
| Result | 1.37 | 1.17 | 1.60 | 1.32 | 0.90 | 1.32 |

The MoR was calculated for each sensitivity sample followed by determination of mean MoR was determined for each run by calculating average of three sets. Run specific Floating cut point was determined as Mean NSB ratio× Normalization factor. 4 PL curve was generated for each sensitivity run by plotting Mean MoR on the y-axis and concentration on the x-axis as represented in FIG. 2. Concentration of run specific Floating cut points was determined by respective curves. Log of the back calculated concentrations was determined and Mean and SD was calculated.

TABLE 10

Back calculation of cut point by sensitivity curves

|  | Result (µg/ml) | Log |
|---|---|---|
| Run-1 | 1.37 | 0.14 |
| Run-2 | 1.17 | 0.07 |
| Run-3 | 1.60 | 0.20 |
| Run-4 | 1.32 | 0.12 |
| Run-5 | 0.90 | −0.05 |
| Run-6 | 1.32 | 0.12 |

Determination of Sensitivity—
Mean=0.10
SD=0.08

$\text{Mean}+t_{0.05\ df}\times SD=0.10+2.015\times 0.08=0.25$

Antilog=1.8 µg/ml
Sensitivity with 95% consistency was determined using the formula $\text{Mean}+t_{0.05 df}\times SD$ where $t_{0.05}$ is the critical value determined from the t-distribution corresponding from 5% false positive rate and 'df' is degrees of freedom (N−1).
Determination of Low Positive Control (LPC):
LPC was determined by the sensitivity data set using formula $-\text{Mean}+t_{0.01\ df}\times SD$ Mean=0.10
SD=0.08

$\text{Mean}+t_{0.01\ df}\times SD=0.10+3.365\times 0.08=0.36$

Antilog=2.3 µg/ml
Positive Controls for the Further Analysis—
High Positive Control (HPC)—4 µg/ml
Low Positive Control (LPC)—2.5 µg/ml
Determination of Assay Precision:
Sensitivity data set was used for establishing assay precision.
Precision was evaluated in following parts—
Intra day precision—Variation between three sets of PC preparations
Inter day precision—Variation between mean of three preparations on three different days
Inter analyst precision—Variation between means of three preparations by two analysts
Overall precision—Variation of all six sets run on each of the three days by two analysts Result:
The imprecision of MoR was calculated and reported as coefficient of variation (CV) and determined by using formula—standard deviation/mean×100.

Precision was determined for HPC (4 µg/ml) and LPC (2 µg/ml)
Precision data is presented in tables 11-13.

TABLE 11 determination of intra day precision
Intra-day variation (CV) of MoR

| NAb | A1, n = 3 | | | A2, n = 3 | | |
|---|---|---|---|---|---|---|
| (µg/ml) | Day-1 | Day-2 | Day-3 | Day-1 | Day-2 | Day-3 |
| 4 | 4 | 14 | 10 | 8 | 8 | 14 |
| 2 | 12 | 15 | 5 | 4 | 1 | 15 |

TABLE 12

Determination of inter day precision
Inter-day variation (CV) of MoR

| | A1 | | | | | | A2 | | | | | |
|---|---|---|---|---|---|---|---|---|---|---|---|---|
| Nab (µg/ml) | Day-1 (n = 3) | Day-2 (n = 3) | Day-3 (n = 3) | Mean | SD | CV | Day-1 (n = 3) | Day-2 (n = 3) | Day-3 (n = 3) | Mean | SD | CV |
| 4 | 1.19 | 1.26 | 0.96 | 1.14 | 0.16 | 14 | 1.10 | 1.18 | 1.02 | 1.10 | 0.08 | 7 |
| 2 | 1.42 | 1.39 | 1.00 | 1.27 | 0.24 | 19 | 1.21 | 1.25 | 1.13 | 1.20 | 0.06 | 5 |

TABLE 13

Determination of overall precision

Overall variation (CV) of MoR
n = 18, days = 3, analysts = 2

| NAb (µg/ml) | Mean | SD | CV |
|---|---|---|---|
| 4 | 1.23 | 0.19 | 15 |
| 2 | 2.30 | 0.28 | 12 |

Precision Summary -

| CV determined for | 2 µg/ml | 4 µg/ml |
|---|---|---|
| Intra Day Precision | ~15 | ~14 |
| Inter day precision | ~19 | ~14 |
| Inter analyst Precision | ~11 | ~6 |
| Overall precision | 15 | 13 |

The assay was found to be precise since both intra and intermediate precision was <20 at both PC levels.
Determination of Assay Specificity:
Rabbit Anti Peptide antibody was spiked in NPHS at HPC and LPC (4 and 2.5 µg/ml) levels and evaluated in the assay along with Anti RHI antibody. Two specificity runs were repeated on two different days.

TABLE 14

Determination of assay specificity

| | Run-1 | | Run-2 | |
|---|---|---|---|---|
| | Anti Peptide | Anti RHI | Anti Peptide | Anti RHI |
| HPC | 2.35 | 1.20 | 2.31 | 1.05 |
| LPC | 2.02 | 0.81 | 2.14 | 1.10 |
| FCP | 1.91 | | 1.48 | |

Rabbit Anti Peptide antibody PC samples were negative in the assay while Anti RHI antibody PC samples were positive for neutralizing activity, thus establishing specificity of the assay for Anti RHI antibody.

Determination of Assay Selectivity:

Selectivity was evaluated with 10 individual normal human serum samples (5 males+5 females) along with normal pooled human serum sample. Each sample was spiked with Anti RHI antibody at LPC and HPC levels and analyzed in the NAb assay. Two runs were performed on two different days.

Result:
i. MoR was determined for each selectivity sample
ii. Floating cut point was determined
iii. Samples with response≤Floating cut point were determined as positive Selectivity data is presented in table 15.

TABLE 15

Determination of assay selectivity

| | | S1 | S2 | S3 | S4 | S5 | S6 | S7 | S8 | S9 | S10 | NPH |
|---|---|---|---|---|---|---|---|---|---|---|---|---|
| Run-1 | HP | 1.08 | 1.07 | 1.01 | 1.01 | 1.00 | 1.12 | 0.99 | 0.90 | 0.98 | 0.93 | 1.04 |
| | LP | 1.10 | 2.66 | 1.19 | 1.02 | 0.98 | 1.91 | 1.00 | 1.04 | 1.05 | 1.94 | 1.05 |
| FCP | | | | | | 1.51 | | | | | | |
| Run-2 | HP | 0.80 | 0.61 | 0.91 | 0.79 | 0.81 | 0.76 | 0.49 | 0.94 | 0.97 | 0.96 | 1.00 |
| | LP | 0.97 | 0.76 | 1.04 | 0.83 | 0.83 | 0.70 | 0.70 | 0.96 | 1.01 | 1.25 | 0.86 |
| FCP | | | | | | 1.25 | | | | | | |

| Summary | Pass | Fail | Total | % Pass |
|---|---|---|---|---|
| HPC | 20 | 0 | 20 | 100 |
| LPC | 17 | 3 | 20 | 85 |

In run-1 and run-2 all the HPC selectivity samples were positive for neutralizing activity 3 of the 10 LPC samples showed negative neutralizing response while all LPC selectivity samples were positive for neutralizing response in run-2. Therefore, 100% of HPC samples and 85% of LPC samples were positive for neutralizing response. LPC and HPC samples prepared in NPHS were positive in both runs.

Determination of Assay Selectivity in Diseased Matrix:

Selectivity in diseased matrix was evaluated by spiking Anti RHI antibody in six individual TI DM patient samples (4 males and 2 females) at HPC and LPC levels.

TABLE 16

Determination of selectivity in T1DM matrix

| | S1 | S2 | S3 | S4 | S5 | S6 | T1 DM Pooled | NPHS |
|---|---|---|---|---|---|---|---|---|
| HPC | 1.36 | 1.20 | 1.20 | 1.13 | 1.35 | 0.93 | 0.87 | 0.91 |
| LPC | 1.43 | 1.26 | 1.37 | 1.09 | 1.57 | 1.18 | 1.01 | 0.98 |
| FCP | | | | | 1.58 | | | |

HPC and LPC samples in six diseased matrices, pooled diseased matrix (pool of 12 individuals) and NPHS showed positive neutralizing response which suggests that assay is selective for detection of Anti RHI detection.

Determination of Drug Tolerance:

$C_{max}$ in Type 1 Diabetes Mellitus patients on RHI therapy is ~100 mU/L which is equivalent to 3.5 ng/ml of RHI. Anti RHI antibody at both levels were complexed with up to 500 ng/ml of RHI which is ~140 fold higher than expected $C_{max}$.

Complexes of HPC and LPC were prepared with 5, 10, 50, 100 and 500 ng/ml of RHI. Evaluation of depletion of RHI and recovery of Anti RHI antibody after sample processing was performed by MSD based RHI assay and ELISA based Anti RHI assay respectively.

Immune complexes (after sample processing) were also evaluated in the neutralizing assay. Two runs were performed on two different days.

In run-1, HPC and LPC were complexed with 10, 100 and 500 ng/ml of RHI while in run-2 HPC and LPC were complexed with 5, 10, 20, 50 and 100 ng/ml of RHI. In both the runs Anti RHI antibody without complex was tested as control.

Evaluation of Depleted RHI:

Depletion of RHI after sample processing was evaluated by MSD based RHI assay. The assay is a sandwich assay where RHI in processed or un-processed samples is captured by Anti RHI monoclonal antibody coated onto the MSD plate and further detected by Sulfo-tag labeled Anti RHI monoclonal antibody. The depletion data of RHI after sample processing is presented in table 17.

TABLE 17

Depletion of RHI by charcoal treatment

| RHI (ng/ml) | Run-1 Result (pg/ml) | Run-2 Result (pg/ml) | Mean (pg/ml) | Mean (ng/ml) |
|---|---|---|---|---|
| 5 | 4045.7 | 5550.9 | 4798.3 | 4.8 |
| 10 | 8827.1 | 9469.0 | 9148.0 | 9.1 |
| 50 | 48591.1 | 48217.1 | 48404.1 | 48.4 |
| 100 | 92608.6 | 89542.3 | 91075.4 | 91.1 |
| 500 | 372785.3 | 418874.3 | 395829.8 | 395.8 |
| HPC + 5 | 506.2 | 157.7 | 332.0 | 0.3 |
| LPC + 5 | 275.6 | BLQ | 275.6 | 0.3 |
| HPC + 10 | 1145.0 | 394.1 | 769.5 | 0.8 |
| LPC + 10 | 586.4 | 292.4 | 439.4 | 0.4 |
| HPC + 50 | 3378.9 | 2642.8 | 3010.8 | 3.0 |
| LPC + 50 | 2329.8 | 1607.7 | 1968.8 | 2.0 |
| HPC + 100 | 3847.1 | 2141.8 | 2994.5 | 3.0 |
| LPC + 100 | 4948.4 | 1152.5 | 3050.5 | 3.1 |
| HPC + 500 | 23971.3 | 17473.6 | 20722.4 | 20.7 |
| LPC + 500 | 19657.9 | 14462.6 | 17060.2 | 17.1 |

The depletion of RHI by charcoal treatment is represented in FIG. 3.

Evaluation of Recovery of NAb after Sample Processing:

Recovery of NAb from immune complexes after processing was determined by Anti RHI ELISA.

TABLE 18

Recovery of NAb after charcoal treatment and illustrated in FIG. 4

| Samples | Result (ng/ml) | Result (µg/ml) |
|---|---|---|
| HPC + 0 | 2438.7 | 2.4 |
| HPC + 5 | 2123.8 | 2.1 |
| HPC + 10 | 2379.6 | 2.4 |
| HPC + 50 | 2163.1 | 2.2 |
| HPC + 100 | 2503.5 | 2.5 |
| HPC + 500 | 1631.2 | 1.6 |
| LPC + 0 | 1072.5 | 1.1 |
| LPC + 5 | 1173.9 | 1.2 |
| LPC + 10 | 1129.6 | 1.1 |
| LPC + 50 | 1087.7 | 1.1 |
| LPC + 100 | 1341.8 | 1.3 |
| LPC + 500 | 902.0 | 0.9 |

Evaluation of Drug Tolerance by Neutralizing Assay:
 i. MoR was determined for each drug tolerance sample.
 ii. Floating cut point was determined
 iii. Sample with MoR≤FCP was determined as positive for neutralizing response against RHI

TABLE 19

Determination of drug tolerance by cell based assay, Run 1

| Run-1 | 0 | 10 ng/ml RHI | 100 ng/ml RHI | 500 ng/ml RHI |
|---|---|---|---|---|
| HPC | 1.38 | 1.12 | 1.46 | 1.02 |
| LPC | 1.29 | 0.93 | 1.66 | 1.73 |
| FCP | | | 1.69 | |

TABLE 20

Determination of drug tolerance by cell based assay, Run 2

| Run-2 | 0 | 5 ng/ml RHI | 10 ng/ml RHI | 20 ng/ml RHI | 50 ng/ml RHI | 100 ng/ml RHI |
|---|---|---|---|---|---|---|
| HPC | 1.05 | 1.02 | 1.13 | 1.09 | 1.11 | 1.34 |
| LPC | 1.10 | 1.19 | 1.04 | 1.10 | 1.16 | 1.31 |
| FCP | | | | 1.48 | | |

More than 90% RHI depletion was observed from the immune complex after sample processing. Recovery of NAb after processing from non-complexed sample was upto 60%, recovery of HPC in presence of 5-100 ng/ml of RHI was ranged between 53-63% but in presence of 500 ng/ml of RHI, recovery was only 41%. Recovery of LPC from complexes with 0-100 ng/ml RHI ranged between 43-54% while that in presence of 500 ng/ml of RHI was only 36%.

Depletion and recovery data correlated with Neutralizing assay data where, in run-1 LPC did not show positive neutralizing response in presence of 500 ng/ml of RHI. HPC was found to tolerate upto 500 ng/ml (16.5 U/Lt) of RHI and LPC upto 100 ng/ml (3.3 U/Lt) of RHI.

The invention claimed is:

1. A method for treating a patient having diabetes, wherein the method comprises utilizing an in vitro method for detecting the presence of recombinant human insulin (rHI) neutralizing antibodies by analyzing a serum sample to alter drug therapy of said patient, the in vitro method comprising the steps of:
 (a) pre-treating the serum sample where the pre-treatment comprises the steps of:
  i. acid dissociation and charcoal treatment;
  ii. neutralization and PEG treatment;
  iii. precipitation of rHI neutralizing antibodies into a pellet; and
  iv. pellet re-suspension;
 (b) a cell-based assay, wherein it comprises the steps of:
  i. seeding of cells having a receptor for rHI;
  ii. starving the cells, wherein starving the cells is carried out for about 18 hours to about 26 hours in a Glucose free medium growth media;
  iii. contacting a population of the cells with rHI and the pre-treated serum sample;
  iv. lysing of the cells and preparing a clear lysate; and
  v. quantifying the phosphorylation of the insulin receptor;
 (c) comparing the amount of phosphorylation with a floating cut point, wherein the floating cut point is characterized as being the amount of phosphorylation of the insulin receptor generally occurring while exhibiting minimal neutralization, wherein the cells have a density ranging from $0.2 \times 10^6$ to $0.5 \times 10^6$ cells per well of a 96 well plate;
 (d) determining that the amount of phosphorylation of the insulin receptor is lower than the floating cut point; and
 (e) increasing amount of drug currently being administered to the patient.

2. The method as claimed in claim 1, wherein acid dissociation comprises treating the serum sample with acetic acid and dextran charcoal solution.

3. The method as claimed in claim 2, wherein the sample of step (a)(i) is treated with acetic acid and dextran charcoal solution and incubated for about 30 minutes at room temperature with shaking at about 180 rpm.

4. The method as claimed in claim 1, wherein neutralization and PEG treatment comprises the steps of:
 i. spinning for about 10 minutes at about 10,000 rpm at about 4° C.;
 ii. transferring the supernatant and adding I M tris buffer and 40% PEG solution; and
 iii. incubating for about 30 minutes at room temperature with orbital shaking at about 180 rpm.

5. The method as claimed in claim 1, wherein pellet re-suspension comprises the steps of:
 i. spinning for about 20 minutes at about 6,000 rpm at about 4° C.;
 ii. discarding the supernatant;
 iii. adding PBS; and
 iv. sonicating for about 10 minutes.

6. The method as claimed in claim 1, wherein the cells are selected from any cell line comprising at least one receptor for the rHI.

7. The method as claimed in claim 6, wherein the cell lines are selected from MCF 10A and MCF-7, human mammary adenocarcinoma cell lines.

8. The method as claimed in claim 6, wherein the cell have a density of $0.2 \times 10^6$ cells per well.

9. The method as claimed in claim 1, wherein the cells are seeded in a DMEM:F12 growth medium and incubated at around 37° C. in humidified air containing about 5% $CO_2$ for a time period of 12 to 16 hours.

10. The method as claimed in claim 1, wherein the step of contacting is carried out for about 5 minutes to about 30 minutes at room temperature in Glucose free DMEM in humidified $CO_2$ incubator.

11. The method as claimed in claim 1, wherein the concentration of rHI is about 10 ng/mL to about 30 ng/mL.

12. The method as claimed in claim 1, wherein lysis is performed in a lysis buffer at room temperature for about 10 minutes.

13. The method as claimed in claim 1, wherein phosphorylation of insulin receptor is detected and quantified using an electrochemiluminescence (ECL) based assay.

14. The method as claimed in claim 1, wherein the determination of floating cut point comprises the steps of:
   i. contacting a population of cells with normal human individual serum samples in presence and absence of rHI;
   ii. determining the magnitude of response for each sample; and
   iii. multiplying the mean of magnitude of response by a normalization factor.

\* \* \* \* \*